(12) United States Patent
Houck (10) Patent No.: US 12,232,869 B2
(45) Date of Patent: Feb. 25, 2025

(54) SENSOR DEVICE

(71) Applicant: VIAVI Solutions Inc., San Jose, CA (US)

(72) Inventor: William D. Houck, Santa Rosa, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 344 days.

(21) Appl. No.: 16/949,156

(22) Filed: Oct. 15, 2020

(65) Prior Publication Data

US 2021/0113123 A1 Apr. 22, 2021

Related U.S. Application Data

(60) Provisional application No. 62/923,247, filed on Oct. 18, 2019.

(51) Int. Cl.
*A61B 5/1455* (2006.01)
*A61B 5/021* (2006.01)
(Continued)

(52) U.S. Cl.
CPC ...... *A61B 5/14551* (2013.01); *A61B 5/02125* (2013.01); *A61B 5/02427* (2013.01); *A61B 5/0261* (2013.01); *G06T 7/0012* (2013.01)

(58) Field of Classification Search
CPC ............ A61B 5/14551; A61B 5/02125; A61B 5/02427; A61B 5/0261; A61B 5/0033;
(Continued)

(56) References Cited

U.S. PATENT DOCUMENTS 8,838,209 B2   9/2014   Mestha et al.
8,897,522 B2   11/2014  Mestha et al.
(Continued)

FOREIGN PATENT DOCUMENTS

CN   103251391 A   8/2013
CN   105792742 A   7/2016
(Continued)

OTHER PUBLICATIONS

Glatter, "Novel Video Camera Can Monitor Your Heart Rate—Using Only Your Face," Forbes, Jan. 30, 2018 [Retrieved from https://www.forbes.com/sites/robertglatter/2018/01/30/novel-video-camera-can-monitor-your-heart-rate-using-only-your-face/#149654f84b9d].
(Continued)

*Primary Examiner* — Eric F Winakur
*Assistant Examiner* — Abid A Mustansir
(74) *Attorney, Agent, or Firm* — Harrity & Harrity, LLP (57) ABSTRACT

Various aspects of the present disclosure generally relate to a multispectral sensor device. In some aspects, a sensor device may obtain, from image data collected by a sensor of the sensor device, first image data regarding a first measurement location of a measurement target, and may obtain, from the image data, second image data regarding a second measurement location of the measurement target, wherein the first measurement location and the second measurement location are sub-surface measurement locations within the measurement target. The sensor device may determine, based on the first image data and the second image data, a pulse transit time measurement, and provide information identifying the pulse transit time measurement. Numerous other aspects are provided.

20 Claims, 7 Drawing Sheets

(51) Int. Cl.
*A61B 5/024* (2006.01)
*A61B 5/026* (2006.01)
*G06T 7/00* (2017.01)

(58) Field of Classification Search
CPC ... A61B 5/0022; A61B 5/443; A61B 5/14552; A61B 5/1032; A61B 5/0075; A61B 5/14546; G06T 7/0012; G06T 2207/10016; G06T 2207/30104; G06T 7/0016

See application file for complete search history.

(56) References Cited

U.S. PATENT DOCUMENTS

| | | | |
|---|---|---|---|
| 11,064,895 B2 | 7/2021 | Onishi et al. | |
| 2009/0245601 A1* | 10/2009 | Cohen | A61B 5/0059 382/128 |
| 2013/0322729 A1 | 12/2013 | Mestha et al. | |
| 2014/0155759 A1* | 6/2014 | Kaestle | A61B 5/0077 600/479 |
| 2014/0276089 A1* | 9/2014 | Kirenko | A61B 5/0077 600/407 |
| 2017/0164904 A1* | 6/2017 | Kirenko | G06T 7/0012 |
| 2018/0055364 A1* | 3/2018 | Pierro | A61B 5/02125 |
| 2020/0288996 A1 | 9/2020 | Yoshizawa et al. | |

FOREIGN PATENT DOCUMENTS

| | | |
|---|---|---|
| EP | 2631874 A1 | 8/2013 |
| JP | 2013169464 A | 9/2013 |
| JP | 2013248386 A | 12/2013 |
| JP | 2019097757 A | 6/2019 |
| WO | 2015078735 A1 | 6/2015 |
| WO | 2018088358 A1 | 5/2018 |
| WO | 2019140155 A1 | 7/2019 |

OTHER PUBLICATIONS

Smith et al., "Pulse transit time: an appraisal of potential clinical applications," Thorax: Occasional Reviews, pp. 452-458, May 1, 1999 [Retrieved from https://thorax.bmj.com/content/54/5/452].

Holz et al, "Glabella: Continuously Sensing Blood Pressure Behavior using an Unobtrusive Wearable Device," Proceedings of the ACM on Interactive, Mobile, Wearable and Ubiquitous Technologies, vol. 1, No. 1, Article 58, Sep. 2017 [Retrieved from https://www.microsoft.com/en-us/research/uploads/prod/2017/09/2017-imwut17-holz_wang-Glabella-Continuously_Sensing_Blood_Pressure_Behavior_using_an_Unobtrusive_Wearable.pdf].

Monakhova et al., "Spectral DiffuserCam: lensless snapshot hyperspectral imaging with a spectral filter array," Sep. 29, 2020 [Retrieved from https://arxiv.org/pdf/2006.08565.pdf].

Fung et al., "Continuous Noninvasive Blood Pressure Measurement by Pulse Transit Time," Proceedings of the 26th Annual International Conference of the IEEE EMBS, San Francisco, CA, Sep. 1-5, 2004, pp. 738-741.

International Search Report and Written Opinion for Application No. PCT/US2020/056137, mailed on Feb. 16, 2021, 11 pages.

* cited by examiner

SENSOR DEVICE

CROSS-REFERENCE TO RELATED APPLICATION

This Patent Application claims priority to U.S. Provisional Patent Application No. 62/923,247, filed on Oct. 18, 2019, and entitled "SENSOR DEVICE." The disclosure of the prior Application is considered part of and is incorporated by reference into this Patent Application.

BACKGROUND

A sensor device may perform measurements for various purposes. For example, the sensor device may determine a measurement based on an interaction with a target. One example of such a target is the human body, for which the sensor device may perform health-related measurements.

SUMMARY

According to some implementations, a method may include obtaining, by a sensor device, from image data collected by a sensor of the sensor device, first image data regarding a first measurement location of a measurement target, obtaining, by the sensor device from the image data, second image data regarding a second measurement location of the measurement target, wherein the first measurement location and the second measurement location are sub-surface measurement locations within the measurement target; determining, by the sensor device and based on the first image data and the second image data, a pulse transit time measurement; and providing, by the sensor device, information identifying the pulse transit time measurement.

According to some implementations, a sensor device may include a sensor and one or more processors, operatively coupled to the sensor, the one or more processors configured to collect image data using the sensor; obtain, from the image data, first image data regarding a first measurement location of a measurement target, obtain, from the image data, second image data regarding a second measurement location of the measurement target, wherein the first measurement location and the second measurement location are sub-surface measurement locations within the measurement target; determine, based on the first image data and the second image data, a pulse transit time measurement; and provide information identifying the pulse transit time measurement.

According to some implementations, a non-transitory computer-readable medium may store one or more instructions. The one or more instructions, when executed by one or more processors of a sensor device, may cause the one or more processors to: obtain first image data regarding a first measurement location of a measurement target and second image data regarding a second measurement location of the measurement target, wherein the first measurement location and the second measurement location are sub-surface measurement locations within the measurement target, and wherein the first image data and the second image data are obtained from a video stream; determine, based on the first image data and the second image data, a pulse transit time measurement; and provide, by the sensor device, information identifying the pulse transit time measurement.

DETAILED DESCRIPTION

The following detailed description of example implementations refers to the accompanying drawings. The same reference numbers in different drawings may identify the same or similar elements. Some aspects of the following description use a spectrometer as an example. However, the measurement principles, procedures, and methods described herein may be used with any sensor, including but not limited to other optical sensors and spectral sensors.

A sensor device may be used to perform health-related measurements, such as blood pressure measurements, blood oxygen measurements (e.g., peripheral capillary oxygen saturation (SpO2) measurements), glucose measurements, surface measurements (e.g., measurements of skin hydration, skin tone, bilirubin levels, and/or the like) and/or the like. Many blood pressure measurement approaches use contact means, such as wearable devices, measurement instrumentation, and/or the like. This provides blood pressure data at a particular point of contact.

It may be beneficial to perform blood pressure measurements at multiple different points (e.g., different spatial points, different points in time, at different depths in a measurement target, and/or the like). Also, it may be beneficial to combine blood pressure measurements with other types of health-related measurements, such as those described above. However, the determination of blood pressure measurements at multiple points using contact means may require a large, costly, and complicated apparatus that can contact multiple points on the measurement target. This may be infeasible for some types of wearable devices or instrumentation. Furthermore, a wearable device or instrumentation may require other contact measurement devices to perform the other types of health-related measurements.

Implementations described herein provide measurement of a measurement target's blood pressure using a pulse transit time measurement, determined using an image sensor of a sensor device. For example, the pulse transit time may be determined with reference to two or more measurement locations on a measurement target, where the two or more locations are included in an image or video stream captured by the image sensor. This may enable the measurement of blood pressure at many different locations on the measurement target. Furthermore, the usage of the image sensor may enable the determination of other health-related measurements at the locations used to determine the pulse transit time measurement and/or at other locations on the surface or under the surface of the measurement target. Thus, implementations described herein provide for examination of optical changes in a volume of tissue that contains blood flow. By using the image sensor to perform such measurements, size, cost, and complexity are reduced relative to a device that uses contact means to perform such measurements. Furthermore, the spacing between measurement locations may be increased relative to a device using contact means, since the device using contact means may need to be at least as large as the distance between the measurement points. Still further, the implementations described herein can perform pulse transit time and/or other measurements for multiple measurement targets (e.g., persons, regions of a person, and/or the like) at once, which may not be possible for a contact-based measurement device.

Figure 1A:
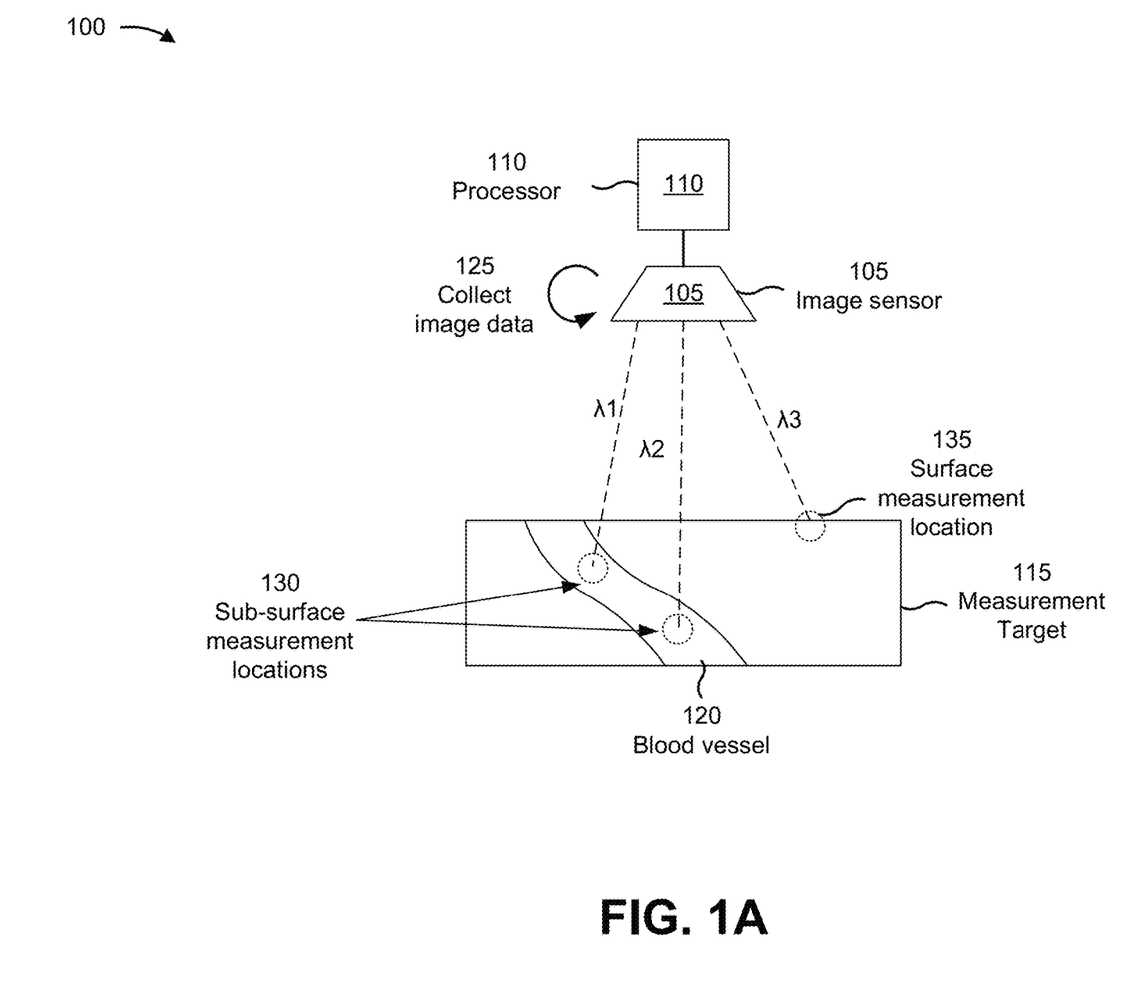
FIGS. 1A and 1B are diagrams of one or more example implementations described herein.
Figure 1B:
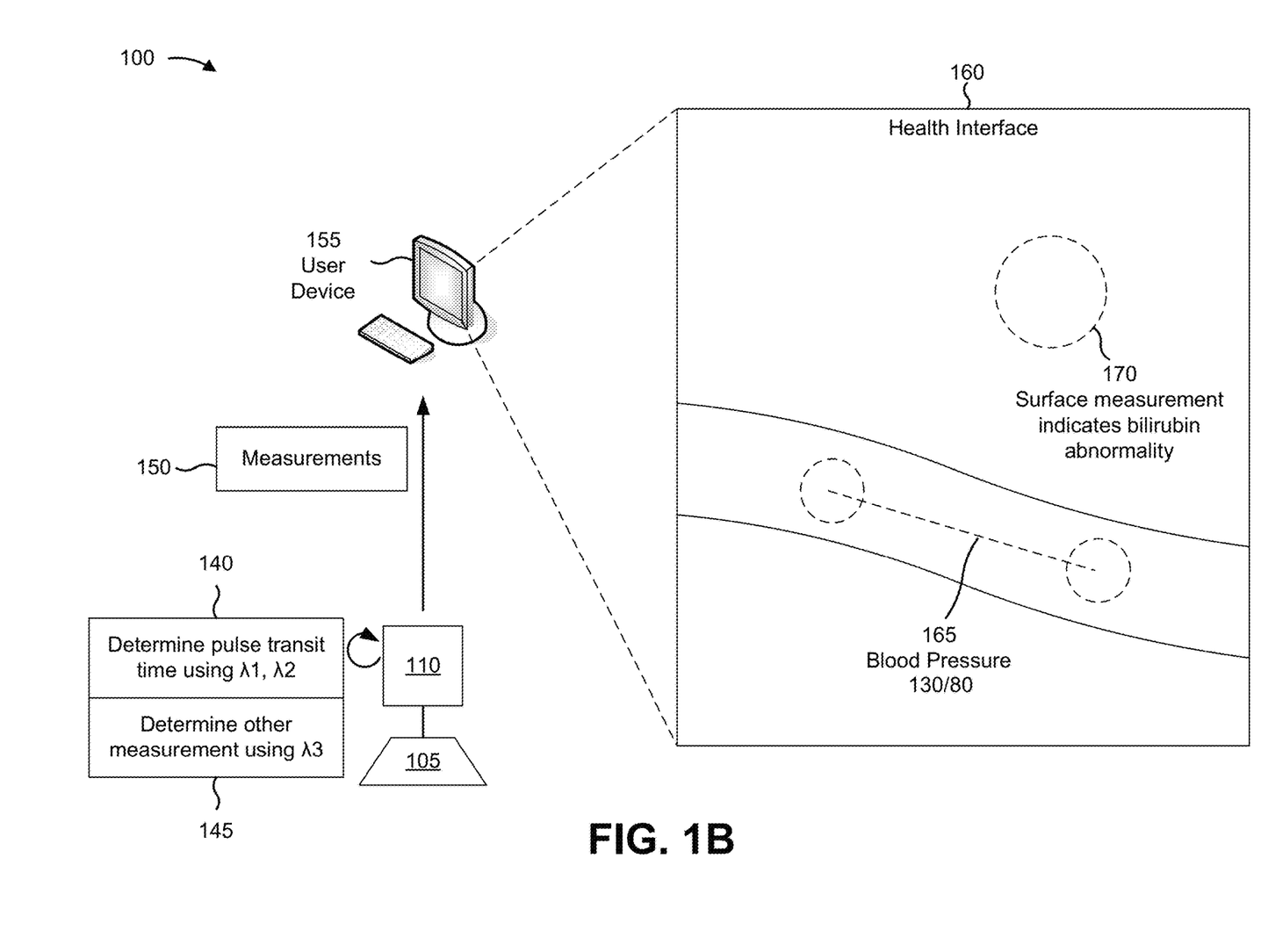

FIGS. 1A and 1B are diagrams of an overview of an example implementation 100 described herein. As shown, example implementation 100 includes an image sensor 105 and a processor 110. The components of image sensor 105 and processor 110 are described in more detail in connection with FIGS. 2 and 3. Image sensor 105 and processor 110 may be associated with a sensor device, which is described in more detail elsewhere herein. References to a sensor device in the description accompanying FIGS. 1A and 1B may refer to one or more of image sensor 105, processor 110, and user device 155 shown in FIG. 1B.

As shown, example implementation 100 includes a measurement target 115. Measurement target 115 may be tissue (e.g., human tissue, animal tissue, and/or the like). As further shown, measurement target 115 may include a blood vessel 120. The sensor device may perform a pulse transit time measurement based on the blood vessel 120, as described below.

As shown by reference number 125, image sensor 105 may collect image data. For example, image sensor 105 may generate a signal for an image stream, a video stream, and/or the like based on receiving light of one or more wavelengths. In some implementations, image sensor 105 may be configured to sense multiple different wavelengths (e.g., $\lambda 1$, $\lambda 2$, and $\lambda 3$ in FIG. 1A), which may enable the determination of different measurements at different measurement locations (e.g., surface measurement locations or sub-surface measurement locations). In some implementations, image sensor 105 may be configured to sense a single wavelength, which may reduce complexity and cost of image sensor 105.

As shown, measurement target 115 may be associated with two sub-surface measurement locations 130. The sensor device may determine a pulse transit time measurement and/or another type of measurement based on the sub-surface measurement locations 130 (e.g., based on information determined using the light associated with 21 and 22), as described in more detail elsewhere herein. In some implementations, measurement target 115 may be associated with any number of sub-surface measurement locations 130. The usage of a larger number of sub-surface measurement locations 130 may provide additional pulse transit time measurements, blood pressure measurements, and/or the like, whereas the usage of a smaller number of sub-surface measurement locations 130 may reduce the complexity and processor usage of the pulse transit time determination. As shown, measurement target 115 may be associated with a surface measurement location 135. The sensor device may perform a health-related measurement based on the light associated with $\lambda 3$ to determine a health parameter, such as a bilirubin content, a temperature, a skin hydration, or another type of health-related parameter. In some implementations, the sensor device may perform the measurements described herein based on a non-contact sensing operation. In a non-contact sensing operation, the sensor device may not be in contact with measurement target 115. For example, the sensor device may be any distance from measurement target 115. Performing the measurement using the non-contact sensing operation may improve versatility of the sensor device and may enable measurements without contacting measurement target 115, which improves safety and efficiency of performing measurements, as described elsewhere herein.

In some implementations, the sensor device may identify the locations 130 and/or 135. For example, the sensor device may identify the locations 130 and/or 135 using a computer vision technique and based on information associated with the image captured by image sensor 105, (e.g., spatial information, a particular wavelength response in the image captured by image sensor 105, and/or the like). In some implementations, the sensor device may identify the locations 130 and/or 135 based on which measurement is to be performed. For example, the sensor device may identify the sub-surface measurement locations 130 for a pulse transit time measurement, a measurement of a health parameter (such as a blood oxygen content measurement (e.g., SpO2) or a heart rate measurement, among other examples), and/or the like, and may identify the surface measurement location 135 for a skin hydration measurement, a bilirubin measurement, and/or the like.

As shown, the sub-surface measurement locations 130 may be associated with wavelengths $\lambda 1$ and $\lambda 2$. In some implementations, $\lambda 1$ and $\lambda 2$ may be the same wavelength. In some implementations, $\lambda 1$ and $\lambda 2$ may be different wavelengths in a same wavelength range. In some implementations, $\lambda 1$ and $\lambda 2$ may be in different wavelength ranges. In some implementations, $\lambda 1$ and/or $\lambda 2$ may be associated with a near-infrared (NIR) range, which may enable taking measurement at sub-surface measurement locations 130. In some implementations, $\lambda 1$ and/or $\lambda 2$ may be associated with another wavelength that can penetrate to a corresponding sub-surface measurement location (e.g., sub-surface measurement location 130).

As shown, the surface measurement location 135 may be associated with a wavelength $\lambda 3$. In some implementations, $\lambda 3$ may be a visible-range wavelength, which may enable color-based measurements and/or the like. Thus, $\lambda 3$ may provide visible-range measurement information regarding the measurement target. In some implementations, $\lambda 3$ may be in a same wavelength range as $\lambda 1$ and/or $\lambda 2$. In some implementations, $\lambda 3$ may be in a different wavelength range than $\lambda 1$ and/or $\lambda 2$. Measurements using $\lambda 3$ in a different wavelength range than $\lambda 1$ and/or $\lambda 2$ may increase the diversity of measurements that can be performed using the sensor device, whereas measurements using $\lambda 3$ in a same wavelength range as $\lambda 1$ and/or $\lambda 2$ may reduce complexity of the sensor device.

While FIG. 1 shows the sensor device receiving light at discrete wavelengths with regard to different measurement locations, it should be understood that the sensor device can receive spectral data associated with multiple wavelengths for a given measurement location. For example, the sensor device may receive light in a frequency range (which may include any one or more of $\lambda 1$ $\lambda 2$, and/or $\lambda 3$, depending on the material properties of the measurement target and/or the measurement locations) with regard to any one or more of the measurement locations shown in FIG. 1 Thus, the sensor device may gather spectrally diverse data measurement associated with multiple different frequencies with regard to a given measurement location. Furthermore, the sensor device may gather spatially diverse measurement data with regard to one or more frequencies at a plurality of different measurement locations. Still further, the sensor device may gather temporally diverse measurement data by performing measurements on spatially and/or spectrally diverse measurement data over time.

As shown in FIG. 1B, and by reference number 140, processor 110 may determine a pulse transit time using $\lambda 1$ and $\lambda 2$. For example, processor 110 may determine the pulse transit time based on measurements at sub-surface measurement locations 130. In some implementations, processor 110 may sample the image data or video stream captured by image sensor 105 (e.g., multiple times per second and/or the like), may identify a pulse at a first sub-surface measurement location 130, and may identify the pulse at the second sub-surface measurement location 130. Based on a time difference (e.g., a number of samples) between identifying the pulse at the first sub-surface measurement location 130 and at the second sub-surface measurement location 130, processor 110 may determine the pulse transit time. In some implementations, processor 110 may determine a blood pressure value based on the pulse transit time. For example, processor 110 may determine the blood pressure value based on a relationship between pulse transit time and blood pressure.

As shown by reference number 145, processor 110 may determine another measurement using the light associated with λ3 (e.g., at the surface measurement location 135). In some implementations, processor 110 may determine the other measurement contemporaneously with determining the pulse transit time measurement. This may enable the determination of temporally correlated health-related measurements, which may provide therapeutic benefits, accuracy benefits, and/or the like. Temporally correlated health-related measurements may be difficult to capture using two or more different sensor devices that are each configured to perform a respective health-related measurement, due to different delays associated with the two or more different sensor devices, difficulty in coordinating operations of the two or more sensor devices, and/or the like. In example implementation 100, the other measurement is a bilirubin measurement (e.g., based on a color associated with the surface measurement location 135, such as a skin color), though the other measurement may include any health-related measurement that can be captured via imaging.

In some implementations, processor 110 may determine a plurality of pulse transit time values based on image data. For example, processor 110 may obtain additional image data regarding one or more other measurement locations, and may determine the plurality of pulse transit time values based on the additional image data. For example, the plurality of pulse transit time values may relate to different regions of the measurement target 115, different blood vessels 120, and/or the like. This may also enable differential measurement of pulse transit times, thereby enabling the detection of discrepancies in pulse transit time, blood pressure, and/or the like at different locations on a measurement target. The determination of pulse transit time values based on image data may also enable the measurement of pulse transit time for multiple, different measurement targets (e.g., multiple, different people) using a single image sensor, since the multiple different measurement targets can be captured in a single image, thereby conserving resources associated with implementing multiple different sensor devices.

As shown by reference number 150, the processor 110 may provide information identifying the measurements determined in connection with reference numbers 140 and 145 to a user device 155. In some implementations, user device 155 may be the sensor device. For example, processor 110 and image sensor 105 may be components of user device 155. In some implementations, user device 155 may be separate from the sensor device.

As shown by reference number 160, user device 155 may provide a visual interface for the health-related measurements determined by the sensor device. Here, the visual interface is shown as a health interface. As shown by reference number 165, the visual interface indicates a blood pressure measurement determined based on the pulse transit time. Furthermore, the visual interface indicates the sub-surface measurement locations used to determine the pulse transit time (e.g., sub-surface measurement locations 130, shown in FIG. 1A). As shown by reference number 170, the visual interface indicates that a bilirubin measurement may be abnormal (e.g., based on a color of the measurement target 115 at the surface measurement location 135 of FIG. 1A). Furthermore, the visual interface indicates the surface measurement location used to determine the bilirubin measurement (e.g., surface measurement location 135, shown in FIG. 1A).

In some implementations, user device 155 may update the visual interface. For example, user device 155 may update a blood pressure measurement based on images captured over time, may provide additional measurements determined based on images captured by the sensor device, and/or the like. In some implementations, user device 155 may provide information based on an interaction with the visual interface. For example, user device 155 may provide additional detail regarding the blood pressure measurement (e.g., the pulse transit time, a heart rate associated with the pulse transit time, additional pulse transit times and/or blood pressures for different measurement locations of the measurement target 115, and/or the like) based on receiving an interaction (e.g., a user interaction and/or the like) with the visual representation of the blood pressure measurement. As another example, user device 155 may modify a measurement location based on an interaction (e.g., an interaction to move the visual representation of the measurement location, an interaction to specify a new location for the measurement location, and/or the like). As yet another example, user device 155 or processor 110 may perform a measurement based on an interaction. For example, the interaction may select the measurement to be performed (e.g., from a menu of available measurements) or may specify a location for the measurement. User device 155 and/or processor 110 may perform the measurement at the location, and may provide information indicating a result of the measurement.

In some implementations, processor 110 may perform a measurement based on a result of another measurement. For example, processor 110 may determine that a blood pressure measurement or a heart rate measurement satisfies a threshold, and may perform another measurement (e.g., a blood oxygen measurement, a body temperature measurement, a skin hydration measurement, and/or the like) based on the blood pressure measurement or the heart rate measurement satisfying the threshold. In some implementations, processor 110 may perform the measurement without user interaction (e.g., automatically), thereby conserving processor resources that would otherwise be used in association with manual triggering of the measurement. In some implementations, processor 110 may provide information identifying the measurement (e.g., via the visual interface, as a notification or alert, and/or the like). In some implementations, processor 110 may trigger an action to be performed based on the measurement (e.g., dispatching a nurse, administering a medication, providing a notification for a user to perform an activity, and/or the like).

In some implementations, processor 110 or user device 155 may determine a blood pressure based on a pulse transit time. For example, processor 110 or user device 155 may determine the blood pressure based on an estimated pressure difference between the measurement locations 130 based on a pulse wave velocity (e.g., by dividing the distance traveled between the measurement locations 130 by the pulse transit time). In some implementations, processor 110 or user device 155 may determine the blood pressure based on the pulse transit time using a different technique than the one described above.

In this way, pulse transit time measurement using an image sensor 105 is performed. Furthermore, additional measurements using the image sensor 105 may be determined in association with (e.g., contemporaneously with) the pulse transit time measurement, thereby enabling temporal correlation of such measurements. Thus, complexity of sensor devices is reduced and flexibility of measurements is improved. Furthermore, the pulse transit time may be performed for any two or more measurement locations at any suitable spacing from each other, thereby improving the usefulness of the pulse transit time data and reducing the mechanical complexity of the sensor device in comparison to a sensor device with contact means for determining the pulse transit time at an adjustable spacing.

In some implementations, image sensor 105 and/or processor 110 may be included in a sensor device such as sensor device 210, described in connection with FIG. 2, below. Sensor device 210 may be capable of sampling spectra across multiple points in a scene and providing an image in which features and locations can be identified to provide multiple points for spectral comparison. Thus, the sensor device can perform a pulse transit time-based blood pressure measurement and/or one or more other measurements described herein. Furthermore, sensor device 210 may provide more flexibility than a device employing sensors at different points in space. For example, sensor device 210 may be capable of performing measurements for multiple users, including users not wearing sensor device 210, and in a non-contact fashion. Furthermore, sensor device 210 may be more resilient to suboptimal sensor placement than devices employing respective sensors at different points in space. For example, sensor device 210 may be capable of capturing an image associated with a field of view (FOV) and may analyze multiple subjects within the FOV, which may be particularly beneficial in a healthcare environment such as a care home, where sensor device 210 may be capable of recognizing and monitoring an individual's health emergency instantaneously while they move within common use spaces. Furthermore, in some implementations, sensor device 210 may perform the operations described herein in a non-contact fashion (e.g., without contacting a measurement target of sensor device 210) and may provide spectral data at multiple points (e.g., every point, a plurality of points) in a scene within the sensor device 210's FOV.

As indicated above, FIGS. 1A and 1B are provided merely as one or more examples. Other examples may differ from what is described with regard to FIGS. 1A and 1B.

Figure 2:
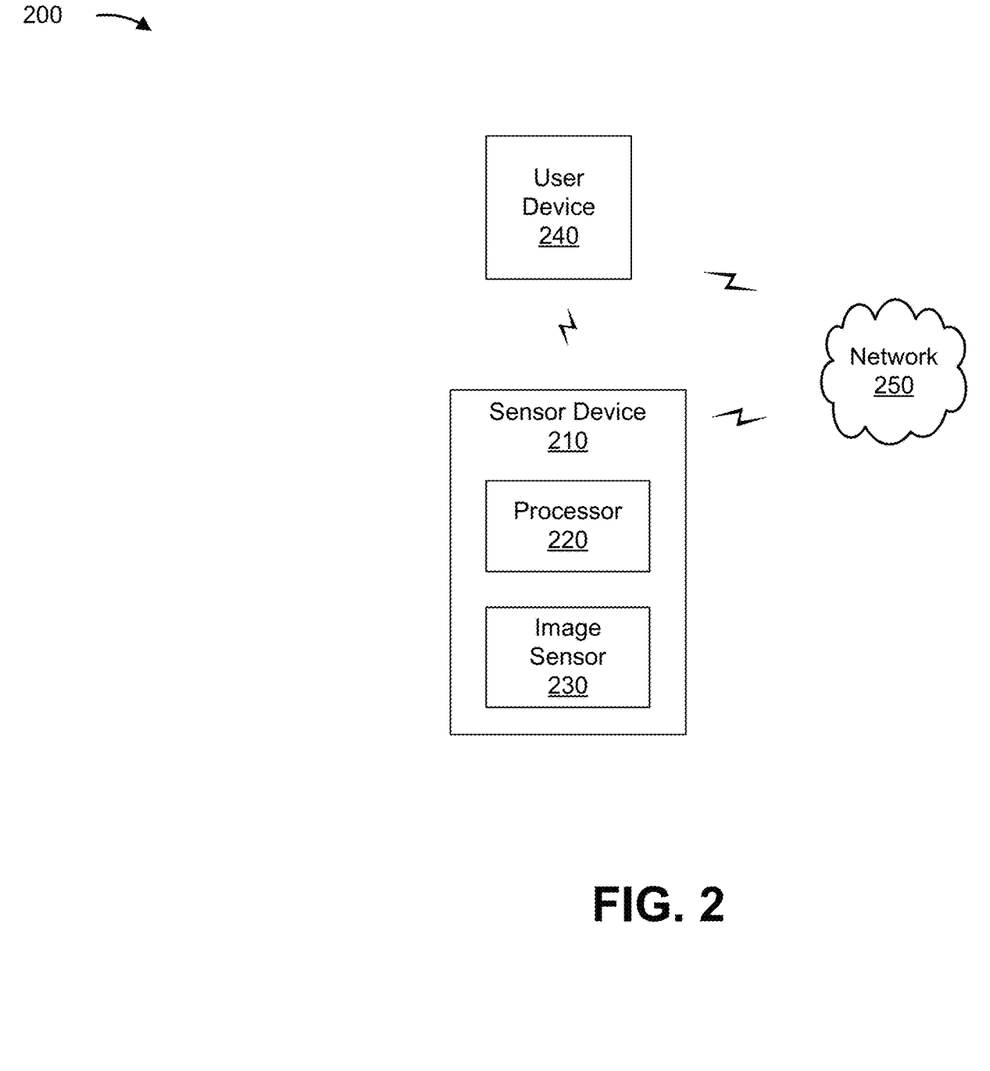
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a user device 240, a network 250, and a sensor device 210 that may include a processor 220 and an image sensor 230. Devices of environment 200 may interconnect via wired connections, wireless connections, or a combination of wired and wireless connections.

Sensor device 210 may include an optical device capable of storing, processing, and/or routing information associated with sensor determination and/or one or more devices capable of performing a sensor measurement on an object. For example, sensor device 210 may include a spectrometer device that performs spectroscopy, such as a spectral sensor device (e.g., a binary multispectral sensor device that performs vibrational spectroscopy, such as a near infrared (NIR) spectrometer, a mid-infrared spectroscopy (mid-IR), Raman spectroscopy, and/or the like). For example, sensor device 210 may perform a health parameter monitoring determination, a pulse transit time determination, a biometric authentication determination, a liveness detection determination, and/or the like. In this case, sensor device 210 may utilize the same wavelengths, different wavelengths, a combination of the same wavelengths and different wavelengths, and/or the like for such determinations. In some implementations, sensor device 210 may be incorporated into user device 240, such as a wearable spectrometer and/or the like. In some implementations, sensor device 210 may receive information from and/or transmit information to another device in environment 200, such as user device 240.

In some implementations, sensor device 210 may comprise a spectral imaging camera. A spectral imaging camera is a device that can capture an image of a scene. A spectral imaging camera (or a processor 220 associated with the spectral imaging camera) may be capable of determining spectral content or changes in spectral content at different points in an image of a scene, such as any point in an image of a scene.

In some implementations, sensor device 210 may comprise a spectral imaging camera capable of performing hyperspectral imaging. For example, sensor device 210 may include a spectral filter array (e.g., a tiled spectral filter array). In some implementations, the spectral filter array may be placed on image sensor 230. In some implementations, sensor device 210 may comprise a diffuser. For example, the diffuser may be configured to diffuse light en route to image sensor 230. Each point in an image captured by sensor device 210 may map to a unique pseudorandom pattern on the spectral filter array, which encodes multiplexed spatio-spectral information. Thus, a hyperspectral volume with sub-super-pixel resolution can be recovered by solving a sparsity-constrained inverse problem. Sensor device 210 can include contiguous spectral filters or non-contiguous spectral filters, which may be chosen for a given application. The usage of the diffuser and the computation approach for determining the hyperspectral volume with sub-super-pixel resolution may improve sampling of spectral content, which enables imaging using a spectral filter such as a hyperspectral filter array. Thus, fabrication of sensor device 210 is simplified in relation to fabrication of a filter on the order of dimension of each pixel. In some implementations, sensor device 210 may comprise a lens.

Sensor device 210 may include a processor 220. Processor 220 is described in more detail in connection with FIG. 3.

Sensor device 210 may include an image sensor 230. Image sensor 230 includes a device capable of sensing light. For example, image sensor 230 may include an image sensor, a multispectral sensor, a spectral sensor, and/or the like. In some implementations, image sensor 230 may include a charge-coupled device (CCD) sensor, a complementary metal-oxide semiconductor (CMOS) sensor, and/or the like. In some implementations, image sensor 230 may include a front-side illumination (FSI) sensor, a back-side illumination (BSI) sensor, and/or the like. In some implementations, image sensor 230 may be included in a camera of sensor device 210 and/or user device 240.

User device 240 includes one or more devices capable of receiving, generating, storing, processing, and/or providing information associated with a sensor determination. For example, user device 240 may include a communication and/or computing device, such as a mobile phone (e.g., a smart phone, a radiotelephone, and/or the like), a computer (e.g., a laptop computer, a tablet computer, a handheld computer, and/or the like), a gaming device, a wearable communication device (e.g., a smart wristwatch, a pair of smart eyeglasses, and/or the like), or a similar type of device. In some implementations, user device 240 may receive information from and/or transmit information to another device in environment 200, such as sensor device 210.

Network 250 includes one or more wired and/or wireless networks. For example, network 250 may include a cellular network (e.g., a long-term evolution (LTE) network, a code division multiple access (CDMA) network, a 3G network, a 4G network, a 5G network, another type of next generation network, and/or the like), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. For example, although sensor device 210 and user device 240 are described as separate devices, sensor device 210 and user device 240 may be implemented as a single device. Additionally, or alternatively, a set of devices (e.g., one or more devices) of environment 200 may perform one or more functions described as being performed by another set of devices of environment 200.

Figure 3:
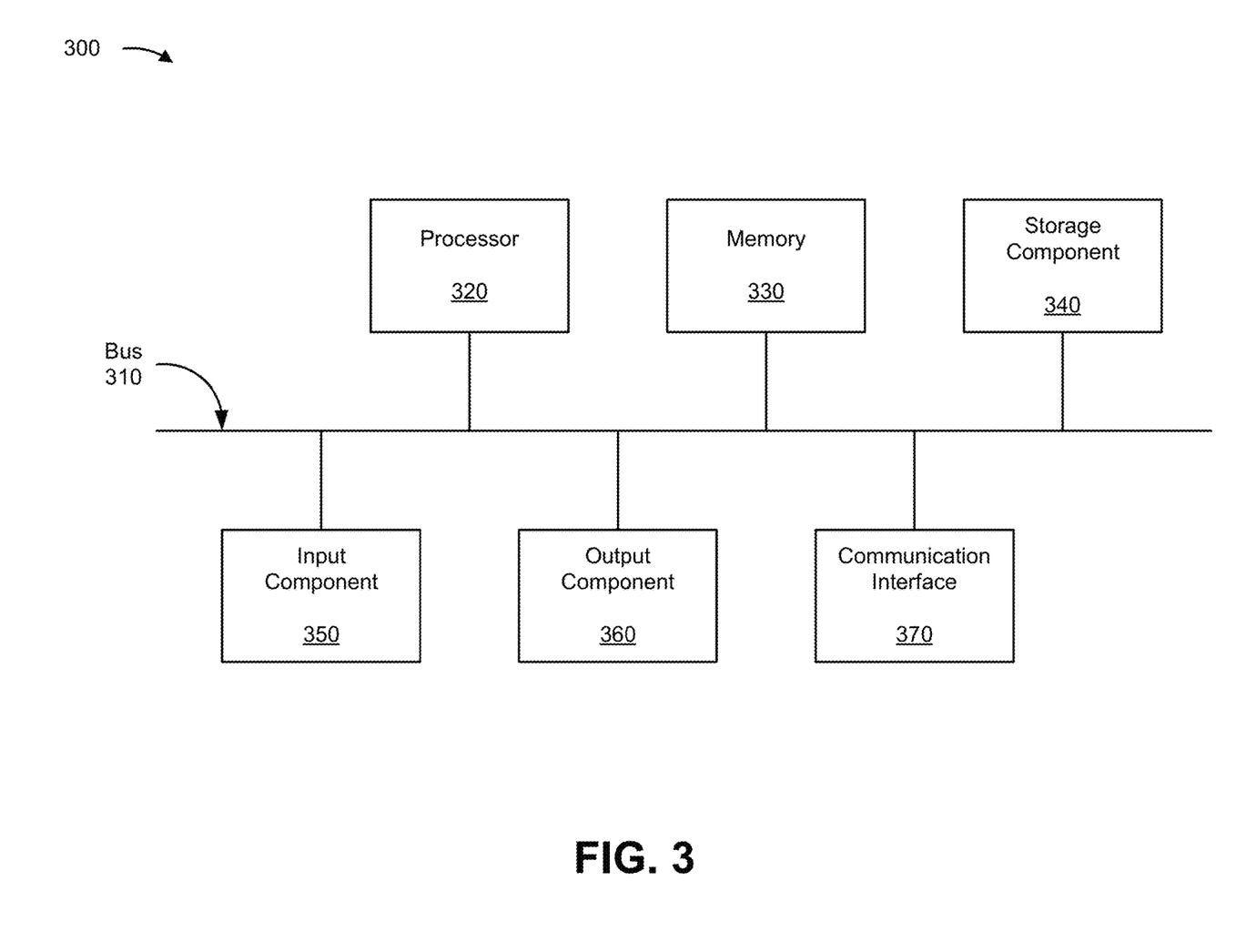
FIG. 3 is a diagram of example components of one or more devices of FIG. 2.

FIG. 3 is a diagram of example components of a device 300. Device 300 may correspond to sensor device 210 and user device 240. In some implementations, sensor device 210 and/or user device 240 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among multiple components of device 300. Processor 320 is implemented in hardware, firmware, and/or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
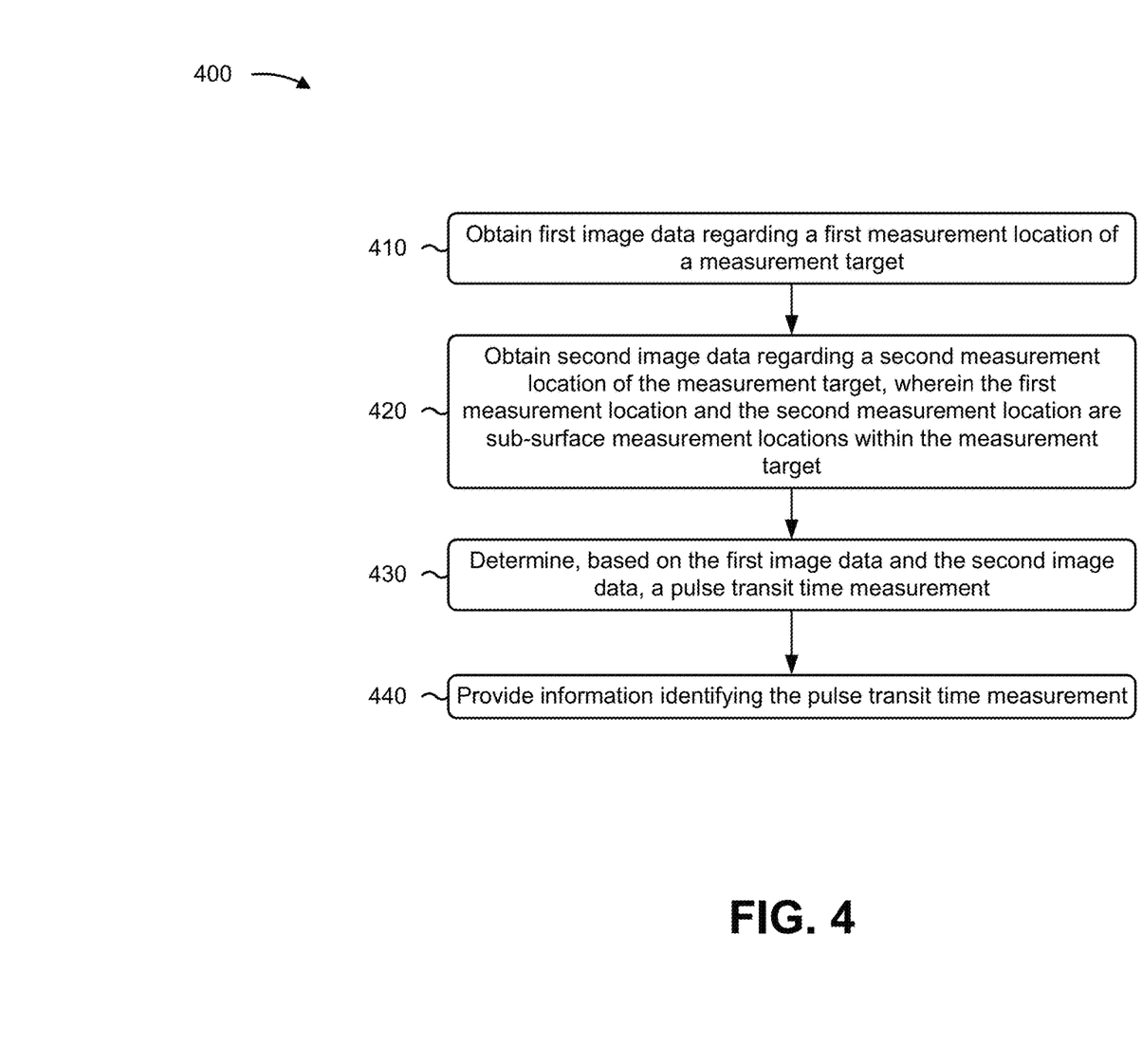
FIGS. 4-6 are flowcharts of example processes for pulse transit time determination using an image sensor.

FIG. 4 is a flow chart of an example process 400 for pulse transit time determination using an image sensor. In some implementations, one or more process blocks of FIG. 4 may be performed by a sensor device (e.g., sensor device 210, the sensor device described in connection with FIG. 1, and/or the like). In some implementations, one or more process blocks of FIG. 4 may be performed by another device or a group of devices separate from or including the sensor device, such as a user device (e.g., user device 155, user device 240, and/or the like) and/or the like.

As shown in FIG. 4, process 400 may include obtaining first image data regarding a first measurement location of a measurement target (block 410). For example, the sensor device (e.g., using processor 320, memory 330, communication interface 370, and/or the like) may obtain first image data regarding a first measurement location of a measurement target, as described above.

As further shown in FIG. 4, process 400 may include obtaining second image data regarding a second measurement location of the measurement target, wherein the first measurement location and the second measurement location are sub-surface measurement locations within the measurement target (block 420). For example, the sensor device (e.g., using processor 320, memory 330, communication interface 370, and/or the like) may obtain second image data regarding a second measurement location of the measurement target, as described above. In some implementations, the first measurement location and the second measurement location are sub-surface measurement locations within the measurement target.

As further shown in FIG. 4, process 400 may include determining, based on the first image data and the second image data, a pulse transit time measurement (block 430). For example, the sensor device (e.g., using processor 320, memory 330, communication interface 370 and/or the like) may determine, based on the first image data and the second image data, a pulse transit time measurement, as described above.

As further shown in FIG. 4, process 400 may include providing information identifying the pulse transit time measurement (block 440). For example, the sensor device (e.g., using processor 320, memory 330, communication interface 370, and/or the like) may provide information identifying the pulse transit time measurement, as described above.

Process 400 may include additional implementations, such as any single implementation or any combination of implementations described below and/or in connection with one or more other processes described elsewhere herein.

In a first implementation, the sensor comprises an image sensor of a camera of the sensor device.

In a second implementation, alone or in combination with the first implementation, process 400 includes determining a blood pressure value using the pulse transit time measurement.

In a third implementation, alone or in combination with one or more of the first and second implementations, the image data includes multispectral image data.

In a fourth implementation, alone or in combination with one or more of the first through third implementations, process 400 includes determining an other measurement, other than the pulse transit time measurement, using the image data.

In a fifth implementation, alone or in combination with one or more of the first through fourth implementations, the other measurement is performed using visible-range information.

In a sixth implementation, alone or in combination with one or more of the first through fifth implementations, the other measurement relates to a skin color of the measurement target.

In a seventh implementation, alone or in combination with one or more of the first through sixth implementations, the other measurement comprises a health parameter.

In an eighth implementation, alone or in combination with one or more of the first through seventh implementations, the health parameter comprises at least one of a heart rate measurement, or an SpO2 measurement.

In a ninth implementation, alone or in combination with one or more of the first through eighth implementations, the first image data and the second image data are associated with a wavelength that penetrates the measurement target to the first measurement location and the second measurement location, respectively.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
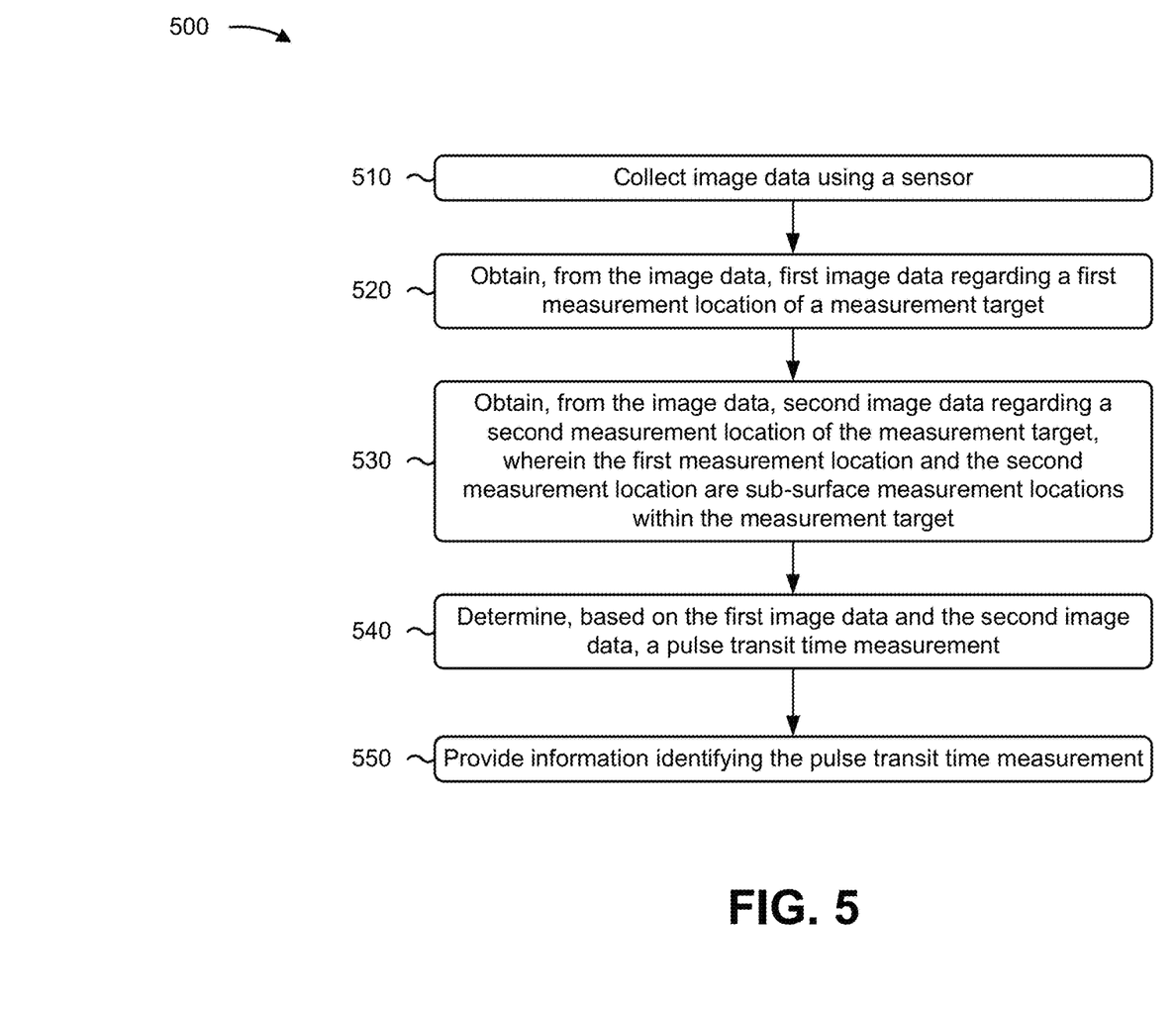

FIG. 5 is a flow chart of an example process 500 for pulse transit time determination using an image sensor. In some implementations, one or more process blocks of FIG. 5 may be performed by a sensor device (e.g., sensor device 210, the sensor device described in connection with FIG. 1, and/or the like). In some implementations, one or more process blocks of FIG. 5 may be performed by another device or a group of devices separate from or including the sensor device, such as a user device (e.g., user device 155, user device 240, and/or the like) and/or the like.

As shown in FIG. 5, process 500 may include collecting image data using the sensor (block 510). For example, the sensor device (e.g., using processor 320, memory 330, communication interface 370, and/or the like) may collect image data using the sensor, as described above.

As further shown in FIG. 5, process 500 may include obtaining, from the image data, first image data regarding a first measurement location of a measurement target (block 520). For example, the sensor device (e.g., using processor 320, memory 330, communication interface 370, and/or the like) may obtain, from the image data, first image data regarding a first measurement location of a measurement target, as described above.

As further shown in FIG. 5, process 500 may include obtaining, from the image data, second image data regarding a second measurement location of the measurement target, wherein the first measurement location and the second measurement location are sub-surface measurement locations within the measurement target (block 530). For example, the sensor device (e.g., using processor 320, memory 330, communication interface 370, and/or the like) may obtain, from the image data, second image data regarding a second measurement location of the measurement target, as described above. In some implementations, the first measurement location and the second measurement location are sub-surface measurement locations within the measurement target.

As further shown in FIG. 5, process 500 may include determining, based on the first image data and the second image data, a pulse transit time measurement (block 540). For example, the sensor device (e.g., using processor 320, memory 330, communication interface 370, and/or the like) may determine, based on the first image data and the second image data, a pulse transit time measurement, as described above.

As further shown in FIG. 5, process 500 may include providing information identifying the pulse transit time measurement (block 550). For example, the sensor device (e.g., using processor 320, memory 330, communication interface 370, and/or the like) may provide information identifying the pulse transit time measurement, as described above.

Process 500 may include additional implementations, such as any single implementation or any combination of implementations described below and/or in connection with one or more other processes described elsewhere herein.

In a first implementation, the first image data and the second image data are based on light generated by the sensor device.

In a second implementation, alone or in combination with the first implementation, the first image data and the second image data are associated with a near-infrared spectral range.

In a third implementation, alone or in combination with one or more of the first and second implementations, process 500 includes obtaining additional image data regarding one or more other measurement locations, and determining one or more other pulse transit time values based on the additional image data.

In a fourth implementation, alone or in combination with one or more of the first through third implementations, an input of the sensor is filtered by the filter based on a binary multispectral technique.

In a fifth implementation, alone or in combination with one or more of the first through fourth implementations, the first image data is associated with a first wavelength that is passed to the sensor and the second image data is associated with a second wavelength that is passed to the sensor.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
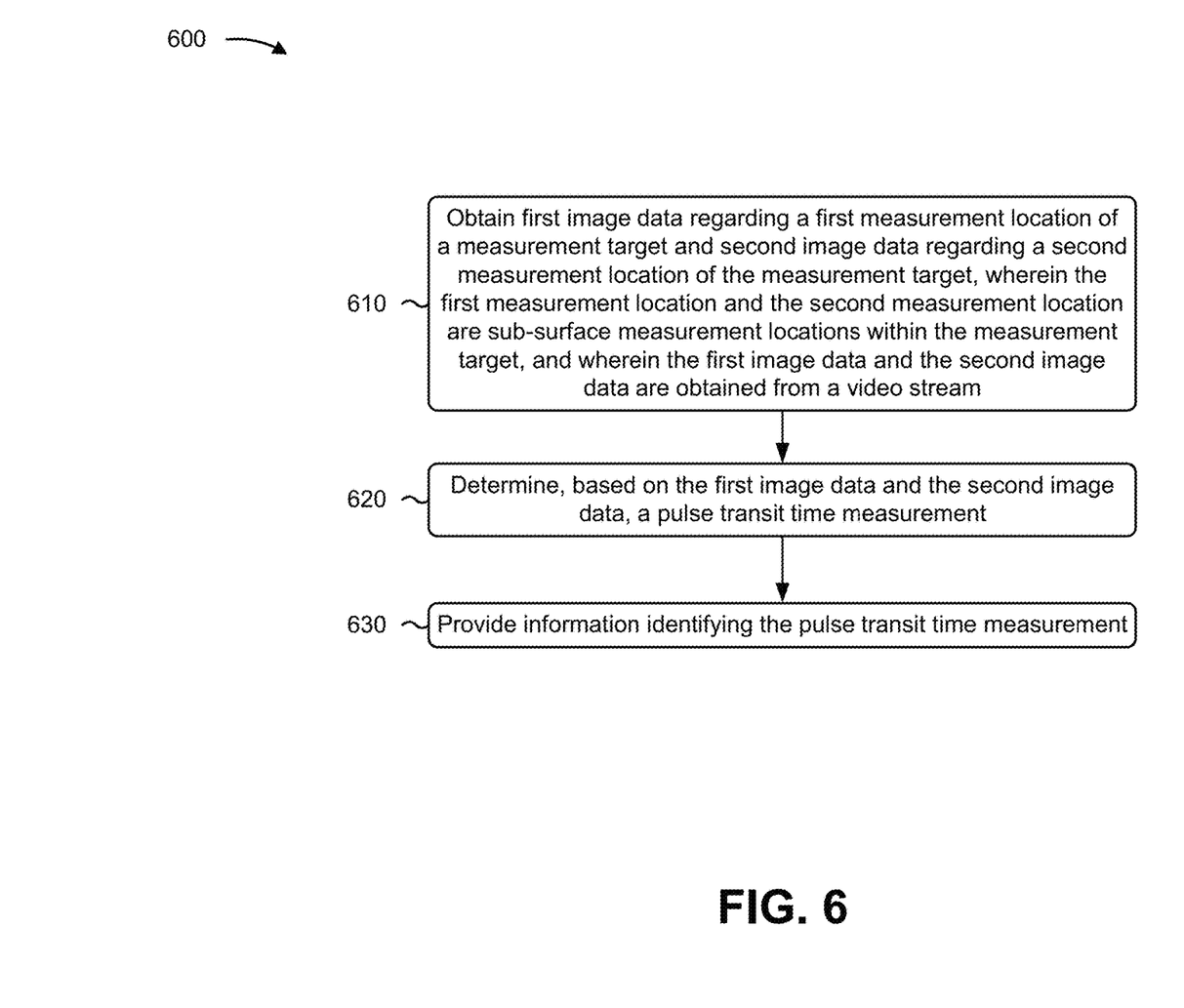

FIG. 6 is a flow chart of an example process 600 for pulse transit time determination using an image sensor. In some implementations, one or more process blocks of FIG. 6 may be performed by a sensor device (e.g., sensor device 210, the sensor device described in connection with FIG. 1, and/or the like). In some implementations, one or more process blocks of FIG. 6 may be performed by another device or a group of devices separate from or including the sensor device, such as a user device (e.g., user device 155, user device 240, and/or the like) and/or the like.

As shown in FIG. 6, process 600 may include obtaining first image data regarding a first measurement location of a measurement target and second image data regarding a second measurement location of the measurement target, wherein the first measurement location and the second measurement location are sub-surface measurement locations within the measurement target, and wherein the first image data and the second image data are obtained from a video stream (block 610). For example, the sensor device (e.g., using processor 320, memory 330, communication interface 370, and/or the like) may obtain first image data regarding a first measurement location of a measurement target and second image data regarding a second measurement location of the measurement target, as described above. In some implementations, the first measurement location and the second measurement location are sub-surface measurement locations within the measurement target. In some implementations, the first image data and the second image data are obtained from a video stream.

As further shown in FIG. 6, process 600 may include determining, based on the first image data and the second image data, a pulse transit time measurement (block 620). For example, the sensor device (e.g., using processor 320, memory 330, communication interface 370, and/or the like) may determine, based on the first image data and the second image data, a pulse transit time measurement, as described above.

As further shown in FIG. 6, process 600 may include providing information identifying the pulse transit time measurement (block 630). For example, the sensor device (e.g., using processor 320, memory 330, communication interface 370, and/or the like) may provide information identifying the pulse transit time measurement, as described above.

Process 600 may include additional implementations, such as any single implementation or any combination of implementations described below and/or in connection with one or more other processes described elsewhere herein.

In a first implementation, the sensor device comprises a smartphone.

In a second implementation, alone or in combination with the first implementation, process 600 includes providing a visual representation of the video stream with information identifying the pulse transit time or information determined based on the pulse transit time.

In a third implementation, alone or in combination with one or more of the first and second implementations, process 600 includes determining another measurement, other than the pulse transit time measurement, using the video stream.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   identifying, by a sensor device, a plurality of measurement locations based on whether a type of measurement that is to be performed is associated with a sub-surface type of measurement location or a surface type of measurement location,
      wherein a first measurement location and a second measurement location, of the plurality of measurement locations, are identified based on the type of measurement that is to be performed is associated with the sub-surface type of measurement location;
   obtaining, by the sensor device, first image data using a wavelength, associated with a near-infrared range, that penetrates to the first measurement location;
   obtaining, by the sensor device, second image data regarding the second measurement location,
      wherein the first measurement location and the second measurement location are different sub-surface measurement locations within a same blood vessel; and
   providing, by the sensor device, information identifying a pulse transit time measurement based on the first image data and the second image data.

2. The method of claim 1, wherein the sensor device comprises a camera that includes an image sensor.

3. The method of claim 1, further comprising:
   determining a blood pressure value using the pulse transit time measurement.

4. The method of claim 1, wherein obtaining the first image data and obtaining the second image data is based on a non-contact sensing operation.

5. The method of claim 1, further comprising:
   determining another measurement, other than the pulse transit time measurement, using image data.

6. The method of claim 5, wherein the other measurement is performed using visible-range information.

7. The method of claim 5, wherein the other measurement relates to a skin color of the same blood vessel.

8. The method of claim 5, wherein the other measurement comprises a health parameter.

9. The method of claim 8, wherein the health parameter comprises at least one of a heart rate measurement or an SpO2 measurement.

10. The method of claim 1, wherein the second image data is obtained using the wavelength, and
    wherein the wavelength further penetrates the same blood vessel to the second measurement location.

11. A sensor device, comprising:
    one or more processors configured to:
       identify a plurality of measurement locations on a measurement target based on whether a type of measurement that is to be performed is associated with a surface on the measurement target or with under the surface,
          wherein a first measurement location and a second measurement location, of the plurality of measurement locations, are identified based on the type of measurement that is to be performed is associated with under the surface;
       obtain first image data using a wavelength, associated with a near-infrared range, that penetrates to the first measurement location;
       obtain second image data regarding the second measurement location,
          wherein the first measurement location and the second measurement location are sub-surface measurement locations within a same blood vessel; and
       provide information identifying a pulse transit time measurement based on the first image data and the second image data.

12. The sensor device of claim 11, wherein the first image data and the second image data are based on light generated by the sensor device.

13. The sensor device of claim 11, wherein the first image data and the second image data are associated with the near-infrared range.

14. The sensor device of claim 11, wherein the one or more processors are further configured to:
    obtain additional image data regarding one or more other measurement locations; and
    determine one or more other pulse transit time values based on the additional image data.

15. The sensor device of claim 11, further comprising:
    a sensor configured to collect image data for the first image data and the second image data,
       wherein an input of the sensor is filtered by a spectral filter array.

16. The sensor device of claim 15, wherein the wavelength is passed to the sensor, and
    wherein the second image data is associated with another wavelength that is passed to the sensor.

17. The sensor device of claim 11, wherein, to identify the plurality of measurement locations, the one or more processors are configured to:

identify the plurality of measurement locations based on a particular wavelength response in a captured image.

18. The sensor device of claim 11, wherein the first measurement location and the second measurement location are associated with the wavelength or with the near-infrared range.

19. The sensor device of claim 11, wherein the second measurement location is associated with a wavelength that is different from the wavelength used to obtain the first image data.

20. A non-transitory computer-readable medium storing instructions, the instructions comprising:

one or more instructions that, when executed by one or more processors of a sensor device, cause the one or more processors to:

identify a plurality of measurement locations based on whether a type of measurement that is to be performed is associated with a sub-surface type of measurement location or a surface type of measurement location, wherein a first measurement location and a second measurement location, of the plurality of measurement locations, are identified based on the type of measurement that is to be performed is associated with the sub-surface type of measurement location;

obtain first image data using a wavelength, associated with a near-infrared range, that penetrates to the first measurement location;

obtain second image data regarding the second measurement location, wherein the first measurement location and the second measurement location are different sub-surface measurement locations within a same blood vessel; and provide information identifying a pulse transit time measurement based on the first image data and the second image data.

* * * * *